United States Patent [19]

Shimamoto et al.

[11] Patent Number: 4,948,786
[45] Date of Patent: Aug. 14, 1990

[54] COMPOSITION FOR TREATMENT OF ISCHEMIC DISORDER IN ORGANS

[75] Inventors: Norio Shimamoto, Hyogo; Kazumi Ogata, Osaka, both of Japan

[73] Assignee: Takeda Chemical Industries, Ltd., Osaka, Japan

[21] Appl. No.: 295,461

[22] Filed: Jan. 10, 1989

[30] Foreign Application Priority Data

Jan. 11, 1988 [JP] Japan .................................. 63-4480

[51] Int. Cl.$^5$ .......................................... A61K 31/665
[52] U.S. Cl. .................................................. 514/100
[58] Field of Search ........................ 549/220; 514/100

[56] References Cited

U.S. PATENT DOCUMENTS 4,564,686 1/1986 Ogata .................................. 549/220

FOREIGN PATENT DOCUMENTS 0202589 11/1986 European Pat. Off. .
0236120 9/1987 European Pat. Off. .

OTHER PUBLICATIONS

Khuzhamberdiev, M. Byull. Eksp. Biol. Med., Chemical Abstracts, vol. 103, 1985, 194288p.
Foye, Principles of Medicinal Chemistry, 2nd Ed., (1981) Lea and Febiger, Philadelphia, pp. 661, 670–678.

Primary Examiner—Mukund J. Shah
Assistant Examiner—E. C. Ward
Attorney, Agent, or Firm—Wegner & Bretschneider

[57] ABSTRACT

The present invention relates to a pharmaceutical composition for the prophylaxis and treatment of ischemic disorder in mammalian organs which contains, as an ingredient, a compound of the formula:

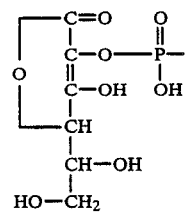

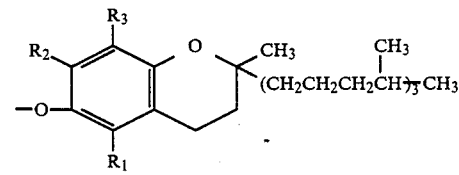

wherein $R_1$, $R_2$ and $R_3$ are independently the methyl group or a hydrogen atom, or a salt thereof.

6 Claims, No Drawings

COMPOSITION FOR TREATMENT OF ISCHEMIC DISORDER IN ORGANS

The present invention relates to a composition for prophylaxis and treatment of ischemic disorder in mammalian organs such as the heart.

Diseases in a mammalian organ such as the heart, brain, kidney, etc., are often observed in adults. This disease is mainly attributed to injury of cells or tissues, which are often caused by ischemia. This injury is caused by lacking of energy supply, which is attributed to decrease or ceasing of blood flow. The aggravation of ischemic tissue, i.e., a decline of cell function, injury of cell wall and destruction or necrosis of cell, etc., depends upon the duration of the ischemia and the sensitivity to the ischemia of organ cells.

Therefore, vasodilators, $\beta$-blockers and calciumantagonists has been used for prophylaxis and treatment of ischemic disorders in mammalian organs up to the present. Vasodilators increase the supply of blood to the organs. $\beta$-blockers and calcium-antagonists reduce the energy demand of organ cells and increase the tolerance of organ cells.

However, it has been revealed by recent research that the formation of lipid peroxide from unsaturated fatty acid, which is a component of the cell wall, and the harmful action of physiologically active metabolites such as prostaglandins, leucotrienes, etc., are deeply concerned with injury of ischemic cells or tissues. Though enormous effort has been devoted to find out and develop new types of drugs based on these recent basic researches, no drug has been found satisfactory. The present inventors have investigated the pharmacological action of phosphoric diester compounds wherein, among the three hydroxyl groups in the phosphoric acid, one hydroxyl group is esterified with the hydroxyl group on the 2-position of ascorbic acid and another hydroxyl group is esterified with the hydroxyl group in one of the tocopherols or their analogs, including $\alpha$-tocopherol. It has been found that these compounds have other specific pharmacological activities, namely the activity to inhibit lipid peroxide formation and a reducing activity of the size of infarction in the ischemia-reperfused rat heart. The present invention was accomplished based on the studies thus far made.

Thus, the present invention provides a composition for the prophylaxis and treatment of ischemic disorders in mammalian organs which contains, as an ingredient, a compound of the formula (I)

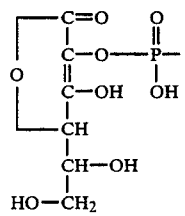

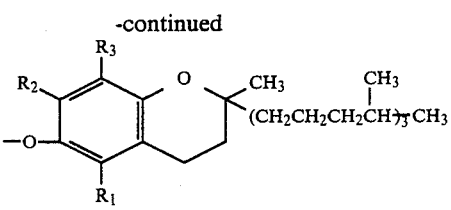

wherein $R_1$, $R_2$ and $R_3$ are independently the methyl group or a hydrogen atom, or a salt thereof.

Among the compounds (I), the compounds wherein at least one of $R_1$ and $R_2$ is the methyl group and $R_3$ is the methyl group are preferable.

The compounds (I) used in the present invention are known compounds as disclosed in the literature and are produced by, for example, reacting $\alpha$-tocopherol with a halogenophosphorylating reagent such as phosphorous oxytrichloride, reacting the resulting product with ascorbic acid wherein the hydroxyl groups in the 5- and 6-positions are protected with a protecting group such as isopropylidene, and removing the protecting groups in the resulting product. The method of producing the compounds (I) is described in detail in U.S. Pat. No. 4,564,686 and EP-A2-0236120.

Alkali metal salts such as the sodium salt and the potassium salt and alkaline earth metal salts such as the calcium salt and the magnesium salt may be exemplified as salts of the compounds (I).

As for the above compounds (I) and the salts thereof, L-ascorbic acid DL-$\alpha$-tocopheryl phosphate diester, its potassium salt, its sodium salt or its calcium salt; L-ascorbic acid DL-$\beta$-tocopheryl phosphate diester or its sodium salt; L-ascorbic acid D-$\gamma$-tocopheryl phosphate diester or its sodium salt; L-ascorbic acid D-$\delta$-tocopheryl phosphate diester or its potassium salt; and L-ascorbic acid DL-tocoryl phosphate diester or its sodium salt may be exemplified.

These compounds have been known as antiinflammatory agents, agents for the prophylaxis and treatment of cataracts and climacteric syndrome, and as ingredients for cosmetics such as those having a skin-beautifying action.

The composition for the prophylaxis and treatment of ischemic disorders in mammalian organs of the present invention contains the above-mentioned compound or salt thereof as an ingredient.

The present composition can be administered orally or parenterally to a mammal such as human beings. The composition may be administered in a form of an injectable solution, a tablet, a capsule or as a syrup by mixing with per se conventional pharmacologically acceptable carriers, i.e., excipients, diluents, etc.

While the dosage varies with the subject, administration routes, symptoms, etc, it is usually administered to an adult human in an amount of more than 0.1 mg/kg body weight one time, usually 5 to 1,000 mg/person, preferably 5 to 300 mg/person 1 to 3 times a day.

The compounds (I) or salts thereof which are the ingredient of the present composition demonstrate the activity to inhibit lipid peroxide formation in vitro by use of brain tissue homogenate and the activity to improve the cardiac disorder in the ischemia-reperfusion rat model. Furthermore, the toxicity of the ingredient of the present composition is extremely low, namely, for example, LD$_{50}$ of L-ascorbic acid DL-$\alpha$-tocopheryl phosphate diester sodium salt is more than 10 g/kg (rat)

by oral administration and 737 mg/kg (rat) by subcutaneous administration.

Therefore, the present composition is useful for prophylaxis and treatment of ischemic heart disease (myocardial infarction, heart failure, arrhythmia, etc.), ischemic disorders of cerebral tissue (cerebral infarction, cerebral apoplexy, etc.) and ischemic renal disorders (renal incompleteness) in mammals such as human beings.

EXAMPLES

The examples are given below to illustrate the present invention more specifically.

In the examples, the compound names are partly abbreviated in the following manner:

α-EPC-Na(DL): L-Ascorbic acid, DL-α-tocopheryl phosphate diester sodium salt [$R_1$, $R_2$, $R_3$=$CH_3$]

β-EPC-K(DL): L-Ascorbic acid DL-β-tocopheryl phosphate diester potassium salt [$R_1$, $R_3$ =$CH_3$, $R_2$=H]

γ-EPC-K(D): L-Ascorbic acid D-γ-tocopheryl phosphate diester potassium salt [$R_1$=H; $R_2$, $R_3$=$CH_3$]

TPC-Na(DL): L-Ascorbic acid DL-tocoryl phosphate diester sodium salt [$R_1$, $R_2$, $R_3$=H]

EXAMPLE 1

Activity of the present compounds to inhibit lipid peroxide formation in rat brain tissue homogenate:

(i) Method:

Male SD rats (10 to 12 weeks old) were subjected to examination under anesthesia with pentobarbital, then the brain tissue was excised. The brain tissue was homogenized in a phosphate buffer solution (pH 7.4) to prepare a 5% homogenate. After incubation of the homogenate at 37° C. for 1 hour, the amount of malonic dialdehyde was determined by the thiobarbituric acid (TBA) method in accordance with the report of Ohkawa et al., in Analytical Biochemistry, 95, 351 (1979). The amount was used as the index of the amount of lipid peroxides formed therein.

The test drug was added to the 5% homogenate before incubation so as to make the final concentration of $10^{-4}$M. The activity to inhibit the formation of lipid peroxide was compared with that of the reference group to which was added the solvent (DMSO), and shown by % inhibition.

(ii) Results:

The results are shown in Table 1 below.

TABLE 1

Inhibitory Effects of the Test Compounds on Lipid Peroxidation in Rat Brain Homogenate

| Compound | Inhibitory Effect (%) | Number of Experiments (n) |
|---|---|---|
| α-EPC-Na(DL) | 61.8 ± 38.1 | (4) |
| β-EPC-K(DL) | 58.9 ± 19.4 | (3) |
| γ-EPC-K-(D) | 62.0 ± 8.2 | (3) |
| δ-EPC-K(D) | 38.1 ± 8.3 | (3) |
| TPC-Na(DL) | 35.7 ± 2.6 | (3) |
| DL-α-tocopherol | 50.8 ± 18.5 | (4) |
| L-ascorbic acid | 1.6 ± 15.0 | (7) |

As shown in the Table 1, the present hydrophylic compounds inhibited lipid peroxidation more than that of α-tocopherol which is lipophylic, and this indicates that the present compound is a useful agent. But L-ascorbic acid per se did not inhibit lipid peroxidation.

EXAMPLE 2

Reducing activity of α-EPC-Na(DL) against the size of infarction in ischemic-reperfused rat heart:

Wistar male rats (body weight 276-3390 g) were anesthetized with pentobarbital and subjected to thoracetomy. The left anterior descending coronary artery (LAD) was ligated at its origin for 1 hour. Then, the ligation was released to allow reperfusion. After 30 to 60 minutes reperfusion, the chest was closed and the animals (rats) maintained in conscious state. After 24 hours, the animals (rats) were reanesthetized, and then the heart was excised. The left ventricles were cut parallel to the atrioventricular sulcus into slices. The slices were stained at 37° C. for 15 minutes using triphenyltetrazolium chloride, and the size of infarction was weighed.

α-EPC-Na dissolved in saline solution was administered into the femoral vein at doses of 0.3, 1 and 5 mg/kg 30 minutes after the ligation. For the control group, only saline solution was administered.

(ii) Results:

The results were shown in Table 2 below:

TABLE 2

Reducing Activity of α-EPC-Na(DL) Against the Size of Infarction in Ischemic-Reperfused Rat Heart

| Dose Amount (mg/kg,i.v.) | Number of Experiments (n) | Size of Infarction (% of left ventrical) | Inhibition (% of Control) |
|---|---|---|---|
| Control | (8) | 35.0 ± 2.9* | |
| α-EPC-Na(DL) | | | |
| 0.3 | (4) | 32.4 ± 4.3 | − 7.4 |
| 1.0 | (5) | 27.2 ± 2.8 | −22.3 |
| 5.0 | (5) | 18.3 ± 1.1 | −47.7 |

*The figures are shown as mean value ± SEM.

As shown in Table 2, it was clarified that α-EPC-Na-(DL) reduced the size of myocardial infarction dose-dependently and to about 50% at a dose of 5 mg/kg.

EXAMPLE 3

Tablets are prepared by the conventional method using the following components:

| L-ascorbic acid DL-α-tocopheryl phosphate acid diester sodium salt | 50 mg |
|---|---|
| Corn starch | 90 mg |
| Lactose | 30 mg |
| Hydroxypropylcellulose | 25 mg |
| Magnesium stearate | 5 mg |
| Total | 200 mg (a tablet) |

EXAMPLE 4

An injectable solution is prepared by the conventional method using the following components:

| L-ascorbic acid D-δ-tocopheryl phosphate diester sodium salt | 20 mg |
|---|---|
| Glucose | 5 mg |
| Distilled water for injection Total | 100 ml |

EXAMPLE 5

Tablets are prepared by the conventional method using the following components:

| | | |
|---|---|---|
| L-ascorbic-acid DL-α-tocopheryl phosphate diester potassium salt | 100 mg | |
| Lactose | 80 mg | |
| Corn starch | 17 mg | |
| Magnesium stearate | 3 mg | |
| Total | 200 mg (a tablet) | |

What is claimed is:

1. A method for the prophylaxis or treatment of ischemic disorder in mammalian organs, which comprises administering to a mammal an effective amount of a compound of the formula:

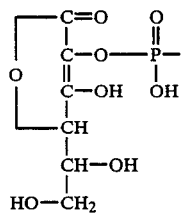

-continued

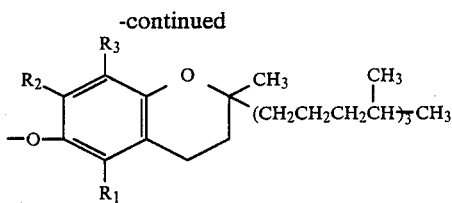

wherein $R_1$, $R_2$ and $R_3$ are independently the methyl group or a hydrogen atom, or a salt thereof.

2. A method according to claim 1, wherein the compound is administered one to three times per day in an amount of 5 to 1,000 mg.

3. A method according to claim 1, wherein at least one of $R_1$ and $R_2$ is methyl and $R_3$ is methyl.

4. A method according to claim 1, wherein the compound is a member selected from the group consisting of L-ascorbic acid DL-α-tocopheryl phosphate diester, its potassium salt, its sodium salt or its calcium salt; L-ascorbic acid DL-β-tocopheryl phosphate diester or its sodium salt; L-ascorbic acid D-τ-tocopheryl phosphate diester or its sodium salt; L-ascorbic acid D-δ-tocopheryl phosphate diester or its potassium salt; and L-ascorbic acid tocoryl phosphate diester or its sodium salt.

5. A method according to claim 1, wherein the compound is L-ascorbic acid DL-α-tocopheryl phosphate diester sodium salt.

6. A method according to claim 1, wherein the ischemic disorder is ischemic heart disease, ischemic disorder of cerebral tissue or ischemic renal disorder.

* * * * *

UNITED STATES PATENT AND TRADEMARK OFFICE
CERTIFICATE OF CORRECTION

PATENT NO. : 4,948,786

DATED : August 14, 1990

INVENTOR(S) : Norio SHIMAMOTO et al.

It is certified that error appears in the above-identified patent and that said Letters Patent is hereby corrected as shown below:

Title page, item (73) Assignee, should read
  --Takeda Chemical Industries, Ltd.,
    Osaka, Japan   and
    Senju Pharmaceutical Co., Ltd.,
    Osaka, Japan --

Signed and Sealed this

Twenty-first Day of January, 1992

Attest:

HARRY F. MANBECK, JR.

*Attesting Officer*          *Commissioner of Patents and Trademarks*